United States Patent [19]

Gardner

[11] 4,079,066

[45] Mar. 14, 1978

[54] 4-NAPHTHYL DERIVATIVES OF 7-AMINOALKYLENOXY-2H-CHROMENE

[75] Inventor: Derek Victor Gardner, Bishops Stortford, England

[73] Assignee: Beecham Group Limited, England

[21] Appl. No.: 652,134

[22] Filed: Jan. 26, 1976

[30] Foreign Application Priority Data

Jul. 19, 1975 United Kingdom .............. 30352/75

[51] Int. Cl.$^2$ ................. C07D 311/02; C07D 207/04; A61K 31/35; A61K 31/40
[52] U.S. Cl. .............................. 260/345.2; 260/239 B; 260/293.58; 260/326.87; 424/244; 424/267; 424/274; 424/283; 424/330; 544/150; 544/151; 544/174; 560/250; 260/293.62; 260/570.7; 424/248.58; 424/248.55
[58] Field of Search ...................... 260/345.2

[56] References Cited

U.S. PATENT DOCUMENTS 3,159,634  12/1964  Jack et al. ........................ 260/570.7
3,388,121  6/1968  Pribyl et al. ...................... 260/570.7

Primary Examiner—Nicky Chan
Attorney, Agent, or Firm—Jacobs & Jacobs

[57] ABSTRACT

Compounds of the formula (I):

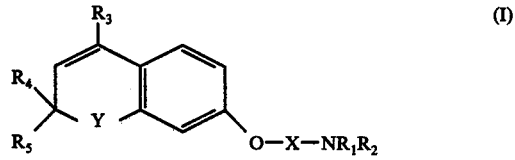

and pharmaceutically acceptable salts thereof wherein X is an alkylene group of 2 - 4 carbon atoms; Y is $CH_2$ or O; $R_1$ is a hydrogen atom or a $C_{1-6}$ alkyl group; $R_2$ is a hydrogen atom or a $C_{1-6}$ alkyl or benzyl group or is joined to $R_1$ so that $NR_1R_1$ is a 5-, 6- or 7- membered saturated ring; $R_3$ is a naphthyl group or a naphthyl group substituted by a fluorine, chlorine or bromine atom or a methyl, methoxyl, trifluoromethyl, hydroxy or acetoxy group; $R_4$ is a hydrogen atom or a $C_{1-4}$ alkyl group; and $R_5$ is a hydrogen atom or a $C_{1-4}$ alkyl group; have been found to be mood modifying agents.

20 Claims, No Drawings

4-NAPHTHYL DERIVATIVES OF 7-AMINOALKYLENOXY-2H-CHROMENE

BACKGROUND TO THE INVENTION

U.S. application Ser. No. 599694, filed July 28, 1975 discloses inter alia that compounds of the formula (II):

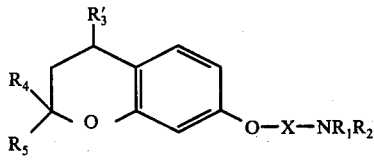
(II)

and their salts wherein X is an alkylene group of 2 - 4 carbon atoms; $R_1$ is a hydrogen atom or a $C_{1-6}$ alkyl group; $R_2$ is a hydrogen atom, a $C_{1-6}$ alkyl, phenyl, tolyl or benzyl group or is linked to $R_1$ so that $NR_1R_2$ is a 5-, 6- or 7- membered saturated ring; $R_3'$ is an aryl or aralkyl group; $R_4$ is a hydrogen atom or a $C_{1-4}$ alkyl group; and $R_5$ is a hydrogen atom or a $C_{1-4}$ alkyl group; possess mood-modifying and anorexia inducing activity.

U.S. application Ser. No. 599694 did not state that corresponding chromenes might possess useful mood-modifying or anorexia inducing activity. However it has now been discovered that certain specific chromenes and tetralenes do possess mood-modifying activity not possessed by the whole class.

DESCRIPTION OF THE INVENTION

It has been discovered that compounds of the formula (I):

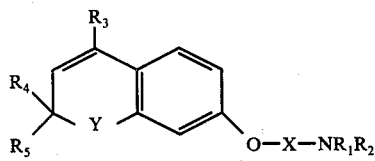
(I)

and pharmaceutically acceptable salts thereof wherein X is an alkylene group of 2 - 4 carbon atoms; Y is $CH_2$ or O; $R_1$ is a hydrogen atom or a $C_{1-6}$ alkyl group; $R_2$ is a hydrogen atom or a $C_{1-6}$ alkyl or benzyl group or is joined to $R_1$ so that $NR_1R_2$ is a 5-, 6- or 7- membered saturated ring; $R_3$ is a naphthyl group or a naphthyl group substituted by a fluorine, chlorine or bromine atom or a methyl, methoxyl, trifluoromethyl, hydroxy or acetoxy group; $R_4$ is a hydrogen atom or a $C_{1-4}$ alkyl group; and $R_5$ is a hydrogen atom or a $C_{1-4}$ alkyl group; have been found to be mood modifying agents.

When used herein the term 'alkylene' group means a divalent alkyl group selected from —$CH_2\cdot CH_2$—, —$CH_2\cdot CH_2\cdot CH_2$—, —$CH(CH_3)\cdot CH_2$—, —$CH_2\cdot CH(CH_3)\cdot CH_2$— or —$CH_2$—$CH(CH_3)$—. The preferred group X is the —$CH_2\cdot CH_2$— group.

Suitable groups $R_1$ include the hydrogen atom and the methyl, ethyl and propyl groups. Suitable groups $R_2$ include the hydrogen atom and the methyl and ethyl groups. Suitable cyclic groups $NR_1R_2$ include the pyrrolidino, piperidino, piperazinyl, N-methylpiperazinyl and morpholino groups. Most suitably $R_1$ is a hydrogen atom or a methyl group. Most suitably $R_2$ is a methyl group.

Most suitably $R_4$ and $R_5$ are hydrogen atoms or methyl groups. Preferably both $R_4$ and $R_5$ are methyl groups. Most suitably Y is an oxygen atom. Most suitably $R_3$ is a naphthyl group. Preferably $R_3$ is a 1-naphthyl group.

One particularly suitable group of compounds of this invention are those of the formula (III):

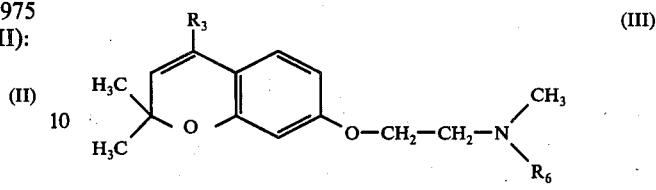
(III)

and salts thereof wherein $R_3$ is as defined in relation to formula (I) and $R_6$ is a hydrogen atom or methyl group.

Suitable groups $R_3$ for inclusion in compounds of the formulae (I) and (III) include 1-naphthyl, 4-chloro-1-naphthyl, 3-chloro-1-naphthyl, 4-fluoro-1-naphthyl and 4-methyl-1-naphthyl and also the slightly less favourable 2-naphthyl and 6-methoxy-2-naphthyl groups.

A preferred group $R_3$ for inclusion in the compounds of the formulae (I) and (III) is the 1-naphthyl group.

Since the compounds of this invention are nitrogenous bases they are able to form acid addition salts in conventional manner. Normally, such salts are those formed from pharmaceutically acceptable organic or inorganic acids such as citric, acetic, propionic, lactic, tartaric, mandelic, succinic, fumaric, oleic, glutamic, gluconic, methanesulphonic, toluenesulphonic, sulphuric, phosphoric, hydrobromic, hydrochloric or the like acid. As will be recognized by those familiar with the formulation of pharmaceutical agents, the nature of the salting acid is relatively unimportant as long as it forms a stable and preferably crystalline pharmaceutically acceptable acid addition salt. Certain compounds within this invention and their salts are able to form solvates such as hydrates, for example, monohydrates.

Compounds within the formula (II) affect the central nervous system. Thus depending on the dosage used, the compounds of the formula (I) are able to produce anorexic or mood modifying effects in mammals.

Accordingly, in one of its aspects the present invention provides pharmaceutical compositions which comprise a compound of this invention as hereinbefore described together with a pharmaceutically acceptable carrier.

Normally, the compositions of this invention are adapted for oral administration to humans although compositions adapted for parenteral administration are also envisaged.

The compositions of this invention may be formulated in conventional manner and with conventional excipients. For example the compositions may be made up into dosage forms similar to those known to be suitable for the administration of mood modifying agents such as tricyclic anti-depressants or benzodiazepinone tranquillizers or the like.

Typical oral formulations will include tablets, pills, capsules, sachets, granules, powders, chewing gum, suspensions, emulsions and solutions. Particularly preferred oral formulations are tablets and capsules. Where appropriate, the formulations may include conventional diluents, binding agents, dispersing agents, surface-active agents, lubricating agents, coating materials, flavouring agents, colouring agents, solvents, thickening agents, suspending agents, sweeteners or any other pharmaceutically acceptable additives, for example, gelatin, lactose, starch, talc, magnesium stearate, hydrogenated oils, polyglycols and syrups. Where the formulations are tablets or capsules and the like, they will represent pre-measured unit doses but in the case of granules, powders, suspensions and the like, the formulations may be presented as pre-measured unit doses or in multi-dose containers from which the appropriate unit dose may be withdrawn.

Unit dosage forms normally contain from 0.1 to 100 mg of active material and may be taken once a day or several times a day according to the dose desired. It is likely that the present compositions will be used as a solid unit dosage from which contains from 0.2 mg to 50 mg of active ingredient, for example, 1mg to 25 mg of active ingredient. Generally a human adult will be administered from 1 to 200 mgs per day, for example, from 5 to 100 mgs.

In a further aspect this invention provides a method of reducing depression, which comprises administering an anti-depressantly effective amount of a compound of this invention.

As an illustration of the activity of the compounds of this invention 2,2-dimethyl-7-(2-dimethylaminoethoxy)-4-(1-naphthyl)-2H-chromene hydrochloride was found to be active on a standard Prevention of Reserpine Induced Hypothermia Test in rats at a dose of about 1 mg/kg when dosed per os (compared to about 3 mg/kg for amitriptyline hydrochloride) and was not found to be lethal to rats at doses below 500 mg/kg when dosed per os.

The compounds of the formula (I) as hereinbefore defined may be prepared by the following processes:

(a) The reaction of a compound of the formula (IV):

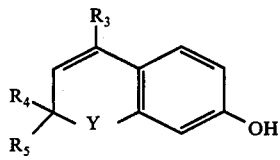
(IV)

or a salt thereof wherein Y, $R_3$, $R_4$ and $R_5$ are as defined in relation to formula (I) with a compound of the formula (V):

$$Q - CH_2CH_2 - NR_1R_2 \qquad (V)$$

or a salt thereof wherein $R_1$ and $R_2$ are as defined in relation to formula (I) and Q is a group readily displaceable by a nucleophile.

(b) The reaction of a compound of the formula (IV):

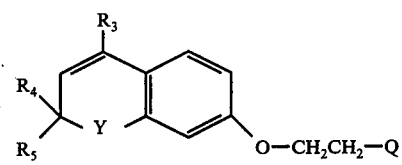
(VI)

wherein Y, $R_3$, $R_4$ and $R_5$ are as defined in relation to formula (I) and Q is a group readily displaced by a nucleophile, with a compound of the formula (VII):

$$HNR_1R_2 \qquad (VII)$$

wherein $R_1$ and $R_2$ are as defined in relation to formula (I).

(c) For those compounds of the formula (I) wherein $R_4$ and $R_5$ are both alkyl groups and Y is an oxygen atom, by the dehydration of a compound of the formula (VIII):

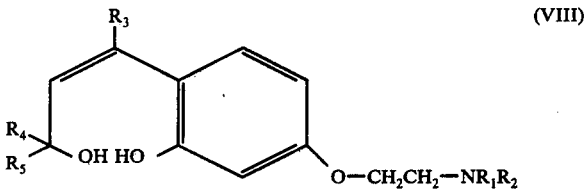
(VIII)

wherein Y, $R_1$, $R_2$ and $R_3$ are as defined in relation to formula (I).

(d) By the dehydration of a compound of the formula (IX):

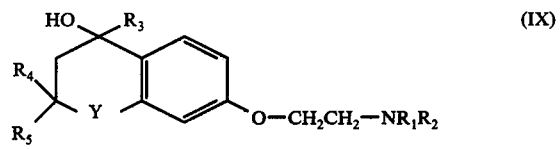
(IX)

or a salt thereof wherein Y, $R_1$, $R_2$, $R_3$ and $R_4$ are as defined in relation to formula (I).

(e) For those compounds of the formula (I) wherein $R_1$ is an alkyl group, by the alkylation of a corresponding compound of the formula (I) or a salt thereof wherein $R_1$ is a hydrogen atom.

(f) The reaction of a compound of the formula (X):

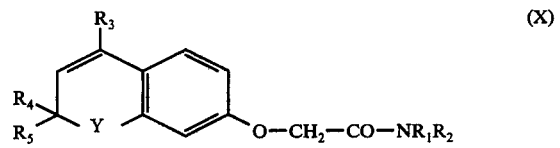
(X)

wherein Y, $R_1$, $R_2$, $R_3$, $R_4$ and $R_5$ are as defined in relation to formula (I), with a complex metal hydride capable of reducing amides to amines.

The reaction of a compound of the formula (IV) or its anion with a compound of the formula (V) is normally carried out in an inert solvent. Suitable solvents include hydrocarbons such as toluene or xylene, ethers such as dimethoxyethane or dimethoxypropane, ketones such as acetone, alcohols such as ethanol and other conventional solvents.

If desired the anion of the compound of the formula (IV) may be produced before the etherification reaction or may be produced in situ by reaction with a base such as NaH or the like.

Generally any non-extreme temperature is used, but the reaction is substantially complete in a conveniently short time if an elevated temperature is used. For example, the reaction may be carried out at from about 0° – 180° C, preferably in the region of 50° – 120° C, for example, at about 70° – 100° C.

Suitable groups Q in the compound of the formula (V) include conventional good leaving groups such as chlorine, bromine or iodine atoms or groups of the formula $O \cdot SO_2R^1$ or $O \cdot CO_2R^1$ where $R^1$ is an inert organic group such as a methyl, ethyl, phenyl, tolyl or like group.

The reaction of the compound of the formula (VI) with an amine of the formula (VII) will normally take place in an inert organic solvent such as a lower alkanol such as methanol, ethanol or the like or a halohydrocarbon such as methylene chloride or chloroform or the like. Such reactions take place at non-extreme temperatures such as -20° - 140° C, and more usually at conventional temperatures such as 0° - 30° C, for example at ambient temperature.

Dehydration of the compounds of the formula (VIII) may be brought about by treatment with an acid catalyst and/or by heating. Generally the reaction takes place in a solvent which is frequently a hydrocarbon solvent. Suitable acid catalysts include mineral acids or stronger organic acids such as toluenesulphonic acid. If the dehydration is promoted by heating it is frequently sufficient to warm the reaction medium to 25° - 100° C.

The dehydration of the compounds of the formula (IX) may take place under similar conditions to those described for the dehydration of compounds of the formula (VIII).

The compounds of the formula (I) wherein $R_1$ is a hydrogen atom are preparable from compounds of the formula (I) wherein $NR_1R_2$ is a group $NR_1^1R_1$ wherein $R_1^1$ is an optionally substituted benzyl group. Such groups include the benzyl, benzhydryl, trityl, methoxybenzyl, halobenzyl, dimethoxybenzhydryl or other equivalent group. Normally the removal of this group is effected by catalytic hydrogenation, for example, using low, medium or high pressures of hydrogen over a transition metal catalyst. It is believed that 1 - 5 atmospheres of hydrogen to be suitable for use in conjunction with a palladium on charcoal catalyst. Normally the reaction is carried out at a non-extreme temperature such as 0° - 100° C, for example, 12° - 80° C; in a conventional solvent such as methanol, ethanol, methyl acetate or the like.

The compounds of the formula (I) wherein $R_1$ and/or $R_2$ are alkyl groups may be prepared by conventional methods of alkylation from corresponding compounds. Reaction with compounds $R_1Q_1$ or $R_2Q_1$ under conventional conditions may be employed but in general are not preferred because they tend to lead to unacceptable side reactions. Particularly suitable methods of alkylation include reductive alkylation using an aldehyde in the presence of a reducing agent. For example, compounds of the formula (I) wherein $R_1$ and/or $R_2$ are methyl groups and may be prepared by reaction with formaldehyde in the presence of formic acid or by reaction with formaldehyde in the presence of a reducing agent such as hydrogen and a transition metal catalyst.

The reduction of a compound of the formula (X) is normally effected using a complex hydride such as lithium aluminium hydride. Such reactions are carried out in an inert solvent medium such as dry ether solvent, for example, in tetrahydrofuran, dioxane, diethyl ether or the like. The reaction may be carried out at any non-extreme temperature, for example, 0° - 120° C and more suitably at an ambient or slightly elevated temperature, for example, at about 15° - 80° C.

Intermediates of the formula (IV) may be prepared by the demethylation of a compound of the formula (XI):

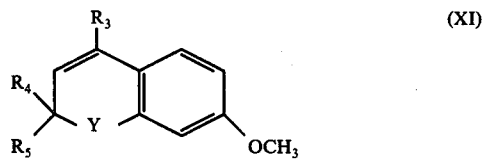

wherein Y, $R_3$, $R_4$ and $R_5$ are as defined in relation to formula (IV).

Demethylation of such a compound may be brought about by the action of a strong acid such as hydriodic acid or hydrobromic acid in conventional manner.

Compounds of the formula (XI) may be prepared by the reaction of a compound of the formula (XII):

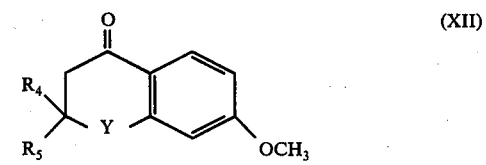

wherein Y, $R_4$ and $R_5$ are as defined in relation to formula (IV) and a metal derivative of the formula $R_3M$ where M is Li, Na, MgI, MgBr or MgCl in conventional manner.

Compounds of the formula (I) wherein Y is an oxygen atom and $R_4$ equals $R_5$ and both are alkyl groups may be prepared by the reaction of $R_4Li$, $R_4MgBr$, $R_4MgI$, $R_4MgCl$ or the chemical equivalent on a compound of the formula (XIII):

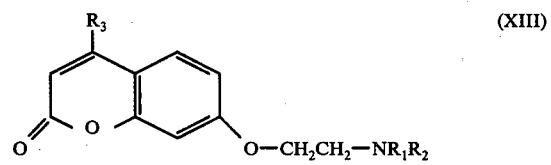

wherein $R_1$, $R_2$, and $R_3$ are as defined in relation to formula (I). Such reactions occur under conventional conditions for Grignard reactions, for example, in an ether solution in the absence of water. As previously indicated the resulting diol frequently dehydrates spontaneously during work up to yield a chromene of the formula (I), especially if heat or acid is involved in the work up.

Compounds of the formula (XIII) may be prepared from the corresponding compound of the formula (XIV):

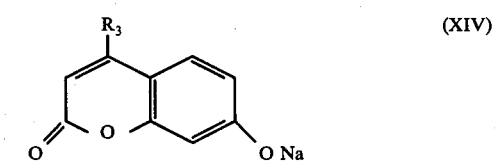

with a compound such as $Cl-CH_2CH_2-NR_1R_2$ at ambient temperature in an alkanolic or similar solvent.

The compounds of the formula (IX) may be prepared by the reaction in a conventional manner of the corresponding compound of the formula (XV):

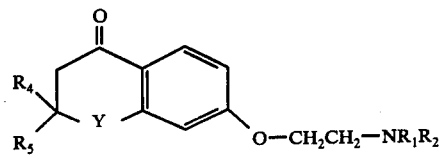

(XV)

wherein Y, $R_1$, $R_2$, $R_4$ and $R_5$ are as defined in relation to formula (I) with a compound of the formula $R_3M$ where M is Li, Na, MgI, MgBr or MgCl.

Such reactions take place in aprotic media, for example, in an ether solvent such as diethyl ether, tetrahydrofuran, dimethoxyethane or the like. The free hydroxy compound is released from its complex by addition of a hydroxylic solvent in conventional manner. Frequently the compound of the formula (IX) is not isolated as work-up causes spontaneous dehydration to yield a chromene of the formula (I).

The compound of the formula (XV) may be prepared from the corresponding compound of the formula (XVI):

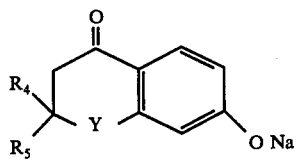

(XVI)

by conventional methods of ether formation such as by reaction of the sodium salt with a compound such as Cl—CH$_2$CH$_2$—NR$_1$R$_2$ at ambient temperature in an alkanolic or similar solvent.

The following Examples illustrate the invention:

EXAMPLE 1

2,2-Dimethyl-7-(2-dimethylaminoethoxy)-4-(1-naphthyl)-2H-chromene hydrochloride 1-Bromonaphthalene (36 g) in dry ether (50 ml) was added to magnesium (4.2 g) in dry ether (50 ml). The solution was refluxed for ½ hour after addition was complete. 2,2-Dimethyl-7-(2-dimethylaminoethoxy)-4-chromanone (15 g) in dry ether (100 ml) was added dropwise and the mixture refluxed for 1 hour. The reaction mixture was poured into ammonium chloride solution extracted with ether and the ether extracts washed with 5N HCl (3 × 100 ml). The acid layer was basified (using concentrated sodium hydroxide solution) and the aqueous layer extracted with ether and the ether layer dried (MgSO$_4$). Removal of the solvent under reduced pressure gave an orange oil (19.6 g) which was chromatographed on alumina (600 g). Elution with ether - petrol (1 : 1) gave an oil (9.1 g) which on treatment with ethereal hydrogen chloride gave the title compound (7.76 g, 33%), m.p. 192°–194° C (ex- acetone).

EXAMPLE 2

2,2-Dimethyl-7-(2-dimethylaminoethoxy)-4-(2-naphthyl)2H-chromene hydrochloride.

m.p. 157°–160° C was obtained in an analogous manner to that described in Example 1.

EXAMPLE 3

2,2-Dimethyl-7-(2-dimethylaminoethoxy)-4-(4-methyl-1-naphthyl)-2H-chromene

To a stirred solution of butyl lithium (12.5 ml, 0.03 mole, 2.4M solution in hexane) was added dropwise over 20 minutes a solution of 1-bromo-4-methylnaphthalene (6.63 g, 0.03 mole) in dry tetrahydrofuran (10 ml), the reaction mixture being cooled throughout by a water bath. After being stirred at ambient temperature for 15 minutes the resulting suspension was treated with a solution of 2,2-dimethyl-7-(2-dimethylaminoethoxy)-4-chromanone (4.0 g, ~0.015 mole) in dry tetrahydrofuran (15 ml), the precipitate almost immediately dissolving to give a golden yellow solution. The resulting solution was stirred under reflux for 5 hours, then left overnight at ambient temperature, stirred under reflux for a further 7 hours and again left overnight at ambient temperature. After work up with acid, by an analogous process to that described in Example 1 and chromatography on alumina in 8% ether - 92% petroleum ether (b.p. 60°–80°) the title compound was obtained as a colourless oil (0.65 g, 11%). Its hydrochloride salt was m.p. 215°–216.5° C.

EXAMPLE 4

4-(4-Fluoro-1-naphthyl)-2,2-dimethyl-7-(2-dimethylaminoethoxy)-2H-chromene

Reaction of 4-fluoro-1-naphthylmagnesium bromide with an equivalent amount of 2,2-dimethyl-7-(2-dimethylaminoethoxy)-4-chromanone in dry tetrahydrofuran, by an analogous method to that described in Example 1 gave the title compound (14%). The hydrochloride salt had m.p. 224.5°–226° C.

EXAMPLE 5

2,2-Dimethyl-7-(2-dimethylaminoethoxy)-4(6-methoxy-2-naphthyl)-2H-chromene a. Ethyl(6-methoxy-2-naphthoyl) acetate To a refluxing mixture of diethylcarbonate (71 g, 0.6 mole) and sodium hydride (44 g, 80% dispersion in oil) in benzene (400 ml) was added dropwise over 3 hours 6-methoxy-2-acetylnaphthalene (60g, 0.3 mole) in benzene (600 ml). After refluxing for 1 hour water was added to the cooled reaction mixture to give the sodium salt of the β-keto ester. The crude product was dissolved in concentrated hydrochloric acid and extracted with ether (3x). The combined ether extracts were dried and removal of the solvent gave ethyl(6-methoxy-2-naphthoyl) acetate (61.0 g, 75%) as a dark coloured oil which partially decomposed to the starting ketone on attempted distillation.

b. 7-Hydroxy-4(6-methoxy-2-naphthyl)coumarin

A stirred solution of ethyl (6-methoxy-2-naphthoyl) acetate (36 g, 0.132 mole), resorcinol (14.6 g, 0.132 mole) and phosphoryl chloride (32 ml) in benzene (200 ml) was refluxed for 3 hours. The reaction mixture was allowed to cool, poured into ice/water and filtered to give the crude product as a red solid. Recrystallization from ethanol gave 7-hydroxy-4(6-methoxy-2-naphthyl)coumarin (28.9 g, 69%) m.p. 223°–225° C.

c. 2,2-Dimethyl-7-hydroxy-4(6-methoxy-2-naphthyl)-2H-chromene

To a solution of methyl lithium (100 ml, 1.9M solution in ether) was added over 0.5 hour 7hydroxy-4(6-methoxy-2-naphthyl)coumarin (6.5g, 0.02 mole). The reaction mixture was stirred for 4 hours, acidified with dilute hydrochloric acid, and stirred for a further 0.5 hour. The organic layer was separated, washed with saturated sodium bicarbonate solution and dried. Removal of the solvent gave 2,2-dimethyl-7-hydroxy-4(6-methoxy-2-naphthyl)-2H-chromene (6.5 g, 96%) as a dark coloured oil which was used in the next reaction without further purification.

d. 2,2-Dimethyl-7-(2-dimethylaminoethoxy)-4(6-methoxy-2-naphthyl)-2H-chromene

To a refluxing solution of 2,2-dimethyl-7-hydroxy-4(6-methoxy-2-naphthyl)2H-chromene (6.4 g, 0.019 mole) and sodium hydride (1.4 g, 80% dispersion in oil) in toluene (150 ml) was added dropwise 2-dimethylaminoethyl chloride (2.7 g, 0.025 mole). After refluxing for 3 hours the solution was cooled and water added. The organic layer was separated and removal of the solvent gave a residue which dissolved in ether and extracted with dilute hydrochloric acid (3x). The combined acid extracts were basified with 40% sodium hydroxide solution and extracted with ether (3x). The combined ether extracts were dried and removal of the solvent gave a quantitative yield of 2,2-dimethyl-7-(2-dimethylaminoethoxy)-4(6-methoxy-2-naphthyl)-2H-chromene which was converted to the hydrochloride salt m.p. 96°-98° C.

EXAMPLE 6

1-(1-naphthyl)-3,4-dihydro-6(2-dimethylaminoethoxy)-naphthalene

1-Naphthylmagnesium bromide was prepared by the addition of 1-bromonaphthalene (9.6 g, 0.046 mole) to magnesium (1 g) in tetrahydrofuran (25 ml). 6-(2-dimethylaminoethoxy)-1-tetralone (9.8 g, 0.046 mole) in tetrahydrofuran 75 ml) was added over ½ hour and the reaction mixture refluxed for 2 hours. After cooling, saturated ammonium chloride solution was added and the organic layer separated. Removal of the solvent gave an oil which after chromatography on alumina, eluting with ether - light petroleum (b.p. 60°-80°) gave 1-(1-naphthyl-3,4-dihydro-6(2-dimethylaminoethoxy)-naphthalene (2.0 g, 15%) as a colourless oil which was converted to the hydrochloride salt m.p. 168°-170° C.

EXAMPLE 7

2,2-Dimethyl-4-(2-naphthyl)-7-[2-(1-piperidino)ethoxy]-2H-chromen (a) 7-Hydroxy-4-(2-naphthyl)coumarin A mixture of resorcinol (11.0 g, 0.1 mole) and ethyl 2-naphthoyl-acetate (24.2 g, 0.1 mole) in concentrated sulphuric acid (50 ml) was stirred at room temperature for 5 days then poured into water to give a yellow gum. The gum was washed several times with water then dissolved in ethanol and diluted with water to give 7-hydroxy-4-(2-naphthyl)coumarin as a fine pale brown precipitate in 26% yield.

(b) 2,2-Dimethyl-4-(2-naphthyl)-2H-chromen-7-ol

To a stirred solution of methyl lithium (0.04 mole, 20 ml of a 1.9M solution in ether) under nitrogen at ambient temperature was added portionwise 7-hydroxy-4-(2-naphthyl)coumarin (2.89 g, 0.01 mole). After 5 hours the solution was decomposed with acid to give 2,2-dimethyl-4-(2-naphthyl)-2H-chromen-7-ol as a crude dark brown foam (2 g) which was used without further purification.

(c) 2,2-Dimethyl-4-(2-naphthyl)-7-[2-(1-piperidino)ethoxy]-2H-chromene

A mixture of 2,2-dimethyl-4-(2-naphthyl)-2H-chromen-7-ol (2.0 g), N-2-chloroethylpiperidino hydrochloride (1.2 g), anhydrous potassium carbonate (2.8 g) and potassium iodide (0.35 g) in anhydrous acetone (16 ml) was stirred under reflux for 4 hours.

The solution was filtered hot and the acetone removed in vacuo. The residue was partitioned between ether - 5N hydrochloric acid and the organic layer was extracted with two further portion of acid. The combined acid extracts were basified and extracted into ether to give a brown gum (2.02 g) which was purified by chromatography on alumina in 12% ether - 88% light petroleum (b.p. 60°-80°) to give the title compound (1.67 g, 61%) as a colourless oil. A portion was converted to the hydrochloride salt, m.p. 226°-229° C (ex acetone).

EXAMPLE 8

7-[2-(N-benzyl-N-methylamino)ethoxy]-2,2-dimethyl-4-(2-naphthyl)-2H-chromene

Reaction of N-benzyl-N-(2-chloroethyl)methylamine hydrochloride with 2,2-dimethyl-4-(2-naphthyl)2H-chromene-7-ol by an analogous method to that described in Example 7 (c) gave the title compound (46%) as a colourless oil, The hydrochloride salt had m.p. 112° - 115° C decomposed.

EXAMPLE 9

7-(2-Diethylaminoethoxy)-2,2-dimethyl-4-(2-naphthyl)-2H-chromene

Reaction of 2-diethylaminoethylchloride hydrochloride with 2,2-dimethyl-4-(2-naphthyl)-2H-chromen-7ol by an analogous method to that described in Example 7 (c) gave the title compound as a colourless oil in 49% yield.

What is claimed is:

1. A compound of the formula (I):

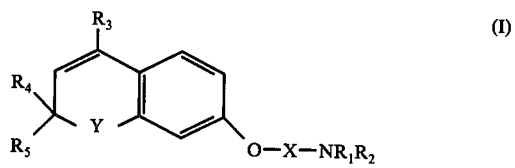

or a pharmaceutically acceptable salt thereof wherein
X is —CH$_2$—CH$_2$—, —CH$_2$—CH$_2$—CH$_2$—, —CH(CH$_3$)—CH$_2$—, —CH$_2$CH(CH)$_3$—CH$_2$— or —CH$_2$—CH(CH$_3$)—;
Y is O;
R$_1$ is hydrogen or alkyl of 1 to 6 carbon atoms;
R$_2$ is hydrogen, alkyl of 1 to 6 carbon atoms or benzyl;
R$_3$ is 1-naphthyl, 4-chloro-1-naphthyl, 3-chloro-1-naphthyl, 4-fluoro-1-naphthyl, 4-methyl-1-naphthyl, 2-naphthyl or 6-methoxy-2-naphthyl;
R$_4$ is hydrogen or alkyl of 1 to 4 carbon atoms; and
R$_5$ is hydrogen or alkyl of 1 to 4 carbon atoms.

2. A compound according to claim 1 wherein R$_1$ is hydrogen or alkyl of 1 to 6 carbon atoms and R$_2$ is hydrogen or alkyl of 1 to 6 carbon atoms.

3. A compound according to claim 1 wherein X is —CH$_2$—CH$_2$.

4. A compound according to claim 1 wherein R$_1$ is hydrogen, methyl, ethyl or propyl and R$_2$ is hydrogen, methyl or ethyl.

5. A compound according to claim 1 wherein R$_1$ is hydrogen or methyl and R$_2$ is methyl.

6. A compound according to claim 1 wherein $R_4$ is hydrogen or methyl and $R_5$ is hydrogen or methyl.

7. A compound according to claim 1 wherein $R_4$ and $R_5$ are each methyl.

8. A compound according to claim 1 in the form of a pharmaceutically acceptable salt wherein said salt is selected from the group consisting of the citrate, acetate, propionate, lactate, tartrate, mandelate, succinate, fumarate, oleate, glutamate, gluconate, methanesulphonate, toluenesulphonate, sulphate, phosphate, hydrobromide and hydrochloride.

9. A compound according to claim 1 in monohydrate form.

10. A compound according to claim 1 wherein $R_3$ is 1-naphthyl.

11. The compound according to claim 1 which is 2,2-dimethyl-7(2-dimethylaminoethoxy)-4(1-naphthyl)-2H-chromene or a pharmaceutically acceptable salt thereof.

12. The compound according to claim 1 which is 2,2-dimethyl-7-(2-dimethylaminoethoxy)-4-(1-naphthyl)-2H-chromene or the hydrochloride salt thereof.

13. The compound according to claim 1 which is 2,2-dimethyl-7-(2-dimethylaminoethoxy)-4-(2-naphthyl)-2H-chromene or the hydrochloride salt thereof.

14. The compound according to claim 1 which is 2,2-dimethyl-7-(2-dimethylaminoethoxy)-4-(4-methyl-1-naphthyl)-2H-chromene.

15. The compound according to claim 1 which is 4-(4-fluoro-1-naphthyl)-2,2-dimethyl-7-(2-dimethylaminoethoxy)-2H-chromene.

16. The compound according to claim 1 which is 2,2-dimethyl-7-(2-dimethylaminoethoxy)-4(6-methoxy-2-naphthyl-2H-chromene.

17. The compound according to claim 1 which is 7-[2-(N-benzyl-N-methylamino)ethoxy]-2,2-dimethyl-4-(2-naphthyl)-2H-chromene.

18. The compound according to claim 1 which is 7-(2-dimethylaminoethoxy)-2,2-dimethyl-4-(2-naphthyl)-2H-chromene.

19. A compound of the formula (III):

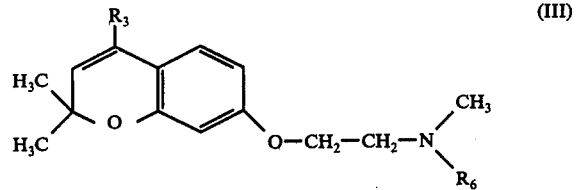

(III)

or a pharmaceutically acceptable salt thereof wherein
$R_3$ is 1-naphthyl, 4-chloro-1-naphthyl, 3-chloro-1-naphthyl, 4-fluoro-1-naphthyl, 4-methyl-1-naphthyl, 2-naphthyl or 6-methoxy-2-naphthyl; and
$R_6$ is hydrogen or methyl.

20. A compound according to claim 19 wherein $R_3$ is 1-naphthyl.

* * * * *